United States Patent [19]

Anzenberger, Sr.

[11] 4,264,534

[45] Apr. 28, 1981

[54] PROCESS FOR REMOVING SOLUBLE METALLIC SALTS FROM A PHOSPHATE ESTER FUNCTIONAL FLUID AND RECLAMATION OF SAID FLUID

[75] Inventor: Joseph F. Anzenberger, Sr., New City, N.Y.

[73] Assignee: Stauffer Chemical Company, Westport, Conn.

[21] Appl. No.: 89,841

[22] Filed: Oct. 31, 1979

Related U.S. Application Data

[62] Division of Ser. No. 947,790, Oct. 2, 1979, Pat. No. 4,205,023.

[51] Int. Cl.$^3$ ................................................. C07F 9/09
[52] U.S. Cl. .................................... 260/990; 260/963; 260/966
[58] Field of Search .............................................. 260/990

[56] References Cited

U.S. PATENT DOCUMENTS

| | | | |
|---|---|---|---|
| 1,866,852 | 7/1932 | Hand et al. | 260/990 |
| 2,358,133 | 9/1944 | Stoesset et al. | 260/990 |
| 2,494,310 | 9/1950 | Pueddemann | 260/990 |
| 2,568,583 | 9/1951 | Graves | 208/180 |
| 2,573,658 | 10/1951 | Weesner | 260/990 |
| 2,716,658 | 8/1955 | Rosin | 260/990 |
| 2,854,468 | 9/1958 | Max | 260/990 |
| 2,976,310 | 3/1961 | Vaughn | 260/990 |
| 3,059,015 | 10/1962 | Pickard et al. | 260/990 |
| 3,219,547 | 11/1965 | Wheeler | 260/990 |
| 3,679,550 | 7/1972 | Orwoll | 260/990 |
| 3,706,822 | 12/1972 | Caldwell et al. | 260/990 |
| 4,092,378 | 5/1978 | Damiani et al. | 260/990 |

FOREIGN PATENT DOCUMENTS

| | | | |
|---|---|---|---|
| 473710 | 5/1955 | Canada | 208/180 |
| 941791 | 11/1963 | United Kingdom | 260/990 |

OTHER PUBLICATIONS

Martell et al., "Chemistry of the Metal Chelate Compounds," Prentice-Hall, Inc. (1956), p. 511.

*Primary Examiner*—Anton H. Sutto
*Attorney, Agent, or Firm*—Michael E. Zall

[57] ABSTRACT

A process is provided for removing soluble metallic salts, such as calcium, copper, zinc, magnesium, tin, iron, or mixtures thereof, from a phosphate ester functional fluid. The process comprises contacting the functional fluid with an effective amount of a chelating agent capable of precipitating at least part of the metallic salts contained therein to form a precipitate, and subsequently separating the precipitate from the functional fluid. A preferred chelating agent is ethylenediaminetetraacetic acid, its alkali metal, alkaline earth or ammonium salts. The process is particularly useful in the reclamation of used triaryl phosphate esters, particularly tert-butylphenyl phenyl phosphates, containing the aforementioned soluble metallic salts.

16 Claims, No Drawings

PROCESS FOR REMOVING SOLUBLE METALLIC SALTS FROM A PHOSPHATE ESTER FUNCTIONAL FLUID AND RECLAMATION OF SAID FLUID

This is a division, of application Ser. No. 947,790 filed Oct. 2, 1979, now U.S. Pat. No. 4,205,023.

BACKGROUND OF THE INVENTION

1. Field of the Invention

This invention relates to a process for removing soluble metallic salts from phosphate ester functional fluids, and in particular to a process for the reclamation of phosphate ester functional fluids.

2. Description of the Prior Art

Many functional fluid systems, such as cooling systems, lubricating systems, hydraulic fluid systems, heat transfer systems, and in particular gas turbine lubricating systems, utilize synthetic phosphate esters, particularly triarylphosphates, as the functional fluid. Triarylphosphates and their use as functional fluids are described in:

U.S. Pat. No. 2,071,023 to Bass;
U.S. Pat. No. 2,938,871 to Matuzzak;
U.S. Pat. No. 3,012,057 to Pierce et al;
U.S. Pat. No. 3,071,549 to Stark;
U.S. Pat. No. 3,468,802 to Nail;
U.S. Pat. No. 3,576,923 to Randall et al;
U.S. Pat. No. 3,723,315 to Sullivan;
U.S. Pat. No. 3,780,145 to Malec;
U.S. Pat. No. 3,931,023 to Dounchis; and
U.S. Pat. No. 3,992,309 to Dounchis.

The entire disclosures of all of the aforementioned patents are incorporated herein by reference.

Generally, after use, phosphate ester functional fluids are discarded or, if attempts are made to reclaim such functional fluids, such attempts are generally ineffective and crude.

Generally, the used functional fluids are contaminated with undesirable metallic salts, such as copper, zinc, magnesium, tin, and iron, salts or mixtures thereof and have an acid number which is too high. Additionally, the used functional fluids contain water, mineral oils and solid contaminants. The combination of soluble metallic salt contamination and high acid number causes corrosion of metallic parts in contact with the functional fluid and autocatalytic oxidation of such metallic parts. Additionally, the soluble metallic salts, for example, copper and zinc, can function as a catalyst in the decomposition of the fluid, particularly at elevated temperatures.

U.S. Pat. No. 3,706,822 issued Dec. 19, 1972 to Caldwell and Sorrell describes a process for refining crude organophosphorus esters comprising washing the ester with a water or aqueous lye solution containing an agent capable of inhibiting the formation of metal ion/partial ester complexes during said washing. These agents include certain chelating agents, and in particular ethylenediaminetetraacetic acid and the sodium, potassium and calcium salts thereof. This refining process, however, is accomplished in an aqueous solution. Such a process applied to the reclamation of used functional fluids would require process steps and equipment to remove the water, for a functional fluid must be substantially free of water.

SUMMARY OF THE INVENTION

An object of this invention is to provide a process for removing soluble metallic salts from phosphate ester functional fluids.

A specific object of this invention to provide a process for the reclamation of used phosphate ester functional fluids which is comparatively simple and utilizes a minimum number of process steps.

Another specific object of this invention is to provide a substantially water-free process for the reclamation of used phosphate ester functional fluids.

It has now been found that the foregoing objects can be attained by the process of this invention. The process is directed to removing soluble metallic salts from a phosphate ester functional fluid. The process comprises contacting the functional fluid with an effective amount of a clelating agent capable of precipitating at least part of the metallic salts contained therein to form a precipitate and subsequently separating the precipitate from the functional fluid. The process is particularly useful in the reclamation of used phosphate ester functional fluids.

DETAILED DESCRIPTION OF THE INVENTION

Broadly the process of this invention has been found to be suitable for use on phosphate ester functional fluids of the general formula:

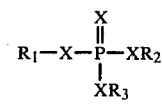

wherein $R_1$, $R_2$ and $R_3$ individually represent an alkyl group, an aryl group, an alkaryl group, an aralkyl group, an alkoxyalkyl group, an alkoxyaryl group, a haloaryl group, a haloalkyl group, a nitroalkyl group, a nitroaryl group, a cyanoaryl group, a haloalkaryl group or an alkyldialkyl group and X represents oxygen, sulfur or a carbon-phosphorus bond, at least two of X being oxygen or sulfur. Hereafter, the use of the term "phosphate ester functional fluid" is intended to include only such compounds as fall within the above definition and which are useful as functional fluids. The functional fluid may contain certain additives to enhance and/or optimize certain properties of the fluid.

The most common phosphate ester functional fluids employed are the triesters of orthophosphoric acid, in particular trialkyl phosphates, triaryl phosphates, and mixed alkyl-aryl phosphates. The esters have the structure:

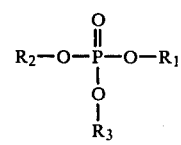

wherein $R_1$, $R_2$ and $R_3$ are each selected from the group consisting of substituted and unsubstituted alkyl and substituted and unsubstituted aryl groups. All three groups may be the same, or all three different, or two groups may be alike and the third different.

The phosphate esters usually have a total carbon content of 3–36 carbon atoms.

The individual alkyl groups usually have 1–12 carbon atoms. Substituted alkyl groups can be employed. The alkyl groups can be substituted with halogens, especially chlorine and fluorine, and with alkoxy groups, i.e. butoxyethyl, benzoxyethyl, 2-chloroethyl and 2-fluoroethyl.

Individual aryl groups usually have 6–12 carbon atoms. Examples of suitable aryl radicals which can be used in the triaryl and mixed aryl phosphates, include phenyl, xylyl, cresyl and halogenated phenyl. A commonly used halogenated aryl material is orthochlorophenyl.

Generic examples of the phosphate esters include trialkyl phosphates, triaryl phosphates and mixed alkaryl phosphates. Specific examples include trimethyl phosphate, tributyl phosphate, dibutyloctyl phosphate, triphenyl phosphate, phenyl dicresyl phosphate, methyl diphenyl phosphate, dibutylphenyl phosphate, t-butylphenyl diphenyl phosphate and tricresyl phosphate.

Synthetic phosphate ester functional fluids generally contain several phosphate esters mixed together. Usually, one particular ester or several closely related esters will predominate.

The process of this invention may be utilized in any situation wherein it is desirable to remove soluble metallic salts from phosphate ester functional fluids. This invention, however, has been found to be particularly suitable for the reclamation of used phosphate ester functional fluids, particularly triaryl phosphate ester functional fluids which have been used in gas turbine lubricating systems. Such fluids are generally contaminated with mixtures of one or more soluble metallic salts, such as copper salts, zinc salts, magnesium salts, tin salts and iron salts, although other salts may be present.

In the process of this invention, the functional fluid is contacted with an effective amount of a chelating agent capable of precipitating at least part of the metallic salts contained therein. It is believed that a chelate/metallic salt/phosphate ester precipitate is formed. The particular metallic salts in the functional fluid determine to some extent the type of chelating agent which is to be utilized. The metallic salts to be precipitated include not only the metallic salts found in the original functional fluid, e.g. the used functional fluid, but also includes any soluble metallic salts produced by any previous process steps, for example, by a process step to reduce the acid number. If for example, as is preferred herein, calcium hydroxide is used to reduce the acid number of a used phosphate ester functional fluid, calcium salts will be added to the functional fluid. The chelating agent should be capable of precipitating these additional calcium salts.

Preferred chelating agents are selected from the group consisting of:
(a) triethanol amine;
(b) ethylenediaminetetraacetic acid;
(c) diethylenetriaminepentaacetic acid;
(d) N-hydroxyethylenediaminetriacetic acid;
(e) the alkali metal, alkaline earth and ammonium salts of (a) through (d); and
(f) mixtures of (a) through (e).

A particularly preferred chelating agent is ethylenediaminetetraacetic acid and the alkali metal alkaline earth and ammonium salts thereof, in particular the diammonium salt and the tetrasodium salt.

A preferred effective amount of such chelating agent is an amount sufficient to complex substantially all of the soluble metallic salts in the functional fluid. Such an amount can be determined by those skilled in the art. It is particularly preferred to utilize a 10.% excess stoichiometric of chelating agent.

When the process is used for the reclamation of used phosphate ester functional fluids, it is preferred that the chelating agent be substantially free of water to eliminate the need for subsequent water removal process steps.

The precipitated metallic salts are separated from the functional fluid. This may be done by methods well known in the art. A particularly preferred method is to filter the functional fluid with a filter aid of, for example, diatomaceous earth.

As indicated previously it is particularly preferred to utilize the process of this invention in the reclamation of used phosphate ester functional fluids. Generally, the used functional fluids, besides having contained therein soluble metallic salts, contain water, mineral oils and solid contaminants. Preferably prior to utilizing the process of this invention for reclamation of such fluids, the fluid is dehydrated, filtered and settled to remove such contaminants. Such processes are well known in the art.

Additionally, the used phosphate ester functional fluid may have an acid number which is too high. This is generally meant to be an acid number greater than about 1.0 mg KOH/g. As used herein, the acid number is measured by ASTM No. D 974. It is desirable to reduce this acid number to an acceptable level, e.g. less than about 1.0 mg KOH/g.

A preferred method of reducing the acid number of the functional fluid is by contacting the fluid with a sufficient amount of a neutralization agent capable of reducing the acid number to an acceptable level. The contacting step is performed by methods well known in the art. A particularly preferred method of contacting is by mixing the neutralization agent in the functional fluid. The neutralization agent is preferably substantially free of water to eliminate the need for subsequent water removal process steps.

Preferred type neutralization agents are alkaline compositions and adsorbent compositions. Preferred alkaline compositions are alkali metal oxides, hydroxides, and carbonates. It has been found that calcium hydroxide and calcium oxide are particularly preferred in that they are capable of reducing high acid numbers to acceptable levels without the use of water. Less effective alkaline compositions may be utilized when the used functional fluid has a low acid number. Preferred adsorbent compositions are fullers earth, activated alumina, bentonites and earth clays.

Generally, an excess amount of neutralization agent is necessary, which necessitates the filtration of the excess neutralization agent from the functional fluid.

The reduction of acid number of the functional fluid is preferably accomplished prior to the process step of contacting the functional fluid with the chelating agent, however, it may also follow such process step.

A particular advantage of this process of reclamation of used functional fluids is that it can be a substantially water free process, thus eliminating the need for subsequent water removal process steps.

The following non-limiting examples serve to illustrate the invention.

EXAMPLE 1

A tert-butylphenyl diphenyl phosphate functional fluid (FYRQUEL ® GT from Stauffer Chemical Company, Westport, Conn.) after being used in a frame 7001 C General Electric gas turbine unit as a lubricating fluid had an acid number of about 2.3 mg KOH/g. The functional fluid was additionally contaminated with soluble copper, zinc and magnesium salts.

16 grams of calcium hydroxide powder was added to 784 grams of the functional fluid. The composition was mixed thoroughly and filtered to remove excess calcium hydroxide. Subsequently, ethylenediaminetetraacetic acid, tetrasodium salt (EDTA) was added to about 400 grams of functional fluid. This amount was sufficient to substantially complex all of the metallic salts (including the calcium salts produced by calcium hydroxide) as precipitates. The precipitate was removed by filtration with diatomaceous earth. The following is a summary of the results:

|  | Used Functional Fluid | Functional Fluid After Treatment With | |
|---|---|---|---|
|  |  | Calcium Hydroxide | Calcium Hydroxide plus EDTA, tetrasodium salt |
| Acid Number, mg KOH/g. | 2.30 | 0.17 | 0.03 |
| Metals Present[1] ppm |  |  |  |
| Cu | 271 | 188 | 6 |
| Zn | 140 | 80 | 0 |
| Mg | 20 | 10 | 0 |
| Ca | 0 | 90 | 0 |
| Na | 0 | — | 165 |

[1] as salts.

EXAMPLE 2

Used tert-butylphenyl diphenyl phosphate functional fluid having an acid number of 2.74 mg KOH/g., was stirred rapidly while 4 g. of calcium hydroxide powder was added. The mixture was warmed to and stirred at 120° to 130° F. (49° to 54° C.) for two hours. A diatomaceous filter aid, 1.5 g., was added and stirring continued for another 15 minutes. The mixture was filtered to obtain a clear product which analyzed as follows:
Acid number—0.18 mg KOH/g.
Copper—121 ppm
Zinc—120 ppm
Calcium—50 ppm The filtrate was stirred rapidly at 100° F. (37.8° C.) and 1 g. of ethylenediaminetetraacetic acid, diammonium salt was added. The mixture was stirred for one hour forming a precipitate which was filtered through diatomaceous filter aid to give a clear filtrate of acid number 0.32 mg KOH/g. The functional fluid contained only 10 ppm of copper.

EXAMPLE 3

Used trixylyl phosphate ester functional fluid (FYRQUEL ® 220) having an acid number of 0.4 mg KOH/g was combined with two weight percent calcium hydroxide and the mixture warmed to and stirred at 120° to 130° F. (49° to 54° C.) for two hours. Diatomaceous filter aid, 0.5 weight percent, was added, the mixture blended for five minutes and filtered. The filtrate analyzed as follows:
Acid number—0.12 mg KOH/g
Iron—10 ppm
Copper—36 ppm
Zinc—50 ppm
Calcium—60 ppm Ethylenediaminetetraacetic acid, diammonium salt, 1.0 weight percent, was added to the filtrate which was warmed to and stirred at 120° to 130° F. (49° to 54° C.) for one forming a precipitate. Diatomaceous filter aid, 0.5 weight percent was added and the mixture stirred another five minutes and filtered. The filtrate had an acid number of 0.34 mg KOH/g. and contained only 38 ppm of copper.

EXAMPLE 4

A used, high acid number (2.7 mg KOH/g) tert-butylphenyl diphenyl phosphate functional fluid containing the following soluble metallic salts:
Copper—271 ppm
Zinc—140 ppm
Magnesium—20 ppm
was treated with 1.0 weight percent of ethylenediaminetetraacetic acid, diammonium salt by stirring the mixture at 130° F. (54° C.) for one hour. A precipitate formed. Diatomaceous earth, 0.5 weight percent, was then added and the mixture stirred for another 15 minutes and filtered. The filtrate was found to contain 16 ppm of sodium.

EXAMPLE 5

A used high acid number (4.4 mg KOH/g) trixylyl phosphate ester functional fluid that was filtered and dehydrated was analyzed and found to contain the following soluble metallic salts:
Iron—50 ppm
Copper—27 ppm
Tin—59 ppm
Silicon—13 ppm
Zinc—30 ppm.

The fluid was treated with ethylenediaminetetraacetic acid, diammonium salt in the same manner as Example 4. A precipitate formed and the fluid was filtered. The filtered fluid was essentially free of all the original soluble metallic salts and contained 6 ppm of iron and 20 ppm of sodium.

What is claimed is:

1. A process for the reclamation of a used phosphate ester functional fluid having an acid number which is too high and contaminated with soluble metallic salts comprising:
    (a) contacting the functional fluid with a sufficient amount of a neutralization agent capable of reducing the acid number to an acceptable level, said neutralization agent being substantially free of water and selected from the group consisting of alkaline compositions and adsorbent compositions;
    (b) contacting the functional fluid with an effective amount of a chelating agent which is substantially free of water, the chelating agent being capable of precipitating at least a portion of the metallic salts contained therein to form a precipitate, and being selected from the group consisting of:
        (i) triethanol amine;
        (ii) ethylenediaminetetraacetic acid;
        (iii) diethylenetriaminepentaacetic acid;
        (iv) N-hydroxyethylenediaminetracetic acid;
        (v) the alkali metal, alkaline earth or ammonium salts of (i) through (iv); and
        (vi) mixtures of (i) through (v);

and subsequently (c) separating the precipitate from the functional fluid.

2. The process of claim 1, wherein the phosphate ester functional fluid is a triaryl phosphate ester.

3. The process of claim 1, wherein the phosphate ester functional fluid is a tert-butylphenyl phenyl phosphate.

4. The process of claim 1, wherein the acid number which is too high is greater than about 1.0 mg KOH/g.

5. The process of claim 4, wherein the acceptable level of the acid number is less than about 1.0 mg KOH/g.

6. The process of claim 1, wherein the metallic salts are calcium salts, copper salts, zinc salts, magnesium salts, tin salts, iron salts, or mixtures thereof.

7. The process of claim 1, wherein the functional fluid is substantially free of water.

8. The process of claim 1, wherein the neutralization agent is an alkaline composition.

9. The process of claim 1, wherein the neutralization agent is an adsorbent composition.

10. The process of claim 1, wherein the chelating agent is ethylenediaminetetraacetic acid.

11. The process of claim 1, wherein the chelating agent is ethylenediaminetetraacetic acid, diammonium salt.

12. The process of claim 1, wherein the chelating agent is ethylenediaminetetraacetic acid, tetrasodium salt.

13. The process of claim 1, wherein the effective amount is an amount sufficient to complex substantially all of the metallic salts in the functional fluid.

14. The process of claim 1, wherein the step of separating is accomplished by filtering with a filter aid.

15. The process of claim 14, wherein the filter aid is diatomaceous earth.

16. A process for the reclamation of a used triarylphosphate ester functional fluid having an acid number greater than about 1.0 mg KOH/g and contaminated with soluble metallic salts of calcium, copper, zinc, magnesium, tin, iron, or mixtures thereof comprising:

(a) contacting the functional fluid with a sufficient amount of an alkaline composition to reduce the acid number to less than about 1.0 mg KOH/g;

(b) contacting the functional fluid with an effective amount of ethylenediaminetetraacetic acid or thereof to form a precipitate, said effective amount being an amount sufficient to complex substantially all of the metallic salts in the functional fluid; and subsequently (c) separating the precipitate from the functional fluid by filtering with a filter aid.

* * * * *

UNITED STATES PATENT AND TRADEMARK OFFICE
CERTIFICATE OF CORRECTION

PATENT NO. : 4,264,534
DATED : April 28, 1981
INVENTOR(S) : Joseph F. Anzenberger, Sr.

It is certified that error appears in the above-identified patent and that said Letters Patent are hereby corrected as shown below:

Under "Related U. S. Application Data" -
 "October 2, 1979" should be -- October 2, 1978 --.

Col. 1, Line 27 - "Pierce" should be -- Fierce --.

Col. 2, Line 18 - "clelating" should be -- chelating --.

In the Claims - Claim 1, Line 65 - "N-hydroxyethylene-diaminetracetic" should be -- N-hydroxyethylene-diaminetriacetic --.

Signed and Sealed this

Twenty-second Day of September 1981

[SEAL]

Attest:

GERALD J. MOSSINGHOFF

*Attesting Officer* — *Commissioner of Patents and Trademarks*